United States Patent
Honda

[19]

[11] Patent Number: 6,066,135
[45] Date of Patent: May 23, 2000

[54] ULTRASONIC OPERATING APPARATUS FOR VIBRATING AN ULTRASONIC VIBRATOR AND PROBE ONLY IN A RANGE CAPABLE OF CONSTANT CURRENT CONTROL AND PLL CONTROL AND A CONTROL METHOD FOR DRIVING ENERGY THEREFOR

[75] Inventor: Yoshitaka Honda, Tokorozawa, Japan

[73] Assignee: Olympus Optical Co., Ltd., Tokyo, Japan

[21] Appl. No.: 09/158,336

[22] Filed: Sep. 22, 1998

[30] Foreign Application Priority Data

Nov. 14, 1997 [JP] Japan .................................. 9-313458

[51] Int. Cl.$^7$ .................................................. A61B 18/18
[52] U.S. Cl. .............................. 606/39; 606/169; 601/2; 607/101
[58] Field of Search ................................. 606/39, 38, 42, 606/169; 601/1–4; 607/101; 604/22

[56] References Cited

U.S. PATENT DOCUMENTS 5,026,387   6/1991   Thomas ................................. 606/169
5,873,873   2/1999   Smith et al. ............................. 606/1
5,897,569   4/1999   Kellogg et al. ........................ 606/169

FOREIGN PATENT DOCUMENTS 2604852   1/1997   Japan .

*Primary Examiner*—Linda C. M. Dvorak
*Assistant Examiner*—David Ruddy
*Attorney, Agent, or Firm*—Frishauf, Holtz, Goodman, Langer & Chick, P.C.

[57] ABSTRACT

An ultrasonic operating apparatus includes an ultrasonic vibrator, an oscillation circuit and a power amplifier which serve as a driving energy supply portion for supplying a driving energy for driving the ultrasonic vibrator. A current detector detects a driving energy supplied to the ultrasonic vibrator. A determining device determines whether or not the ultrasonic vibrator is driven normally depending on whether or not the current component of the driving energy detected by the current detector is in a predetermined range. If it is determined that the ultrasonic vibrator is not driven normally, a stop device stops a supply of the driving energy to the ultrasonic vibrator.

10 Claims, 10 Drawing Sheets

|  | OUTPUT A | OUTPUT B | OUTPUT C |
|---|---|---|---|
| $|I| > 23a$ | L | H | L |
| $23a \geq |I| \geq 23b$ | H | H | H |
| $23b > |I|$ | H | L | L |
FIG. 7
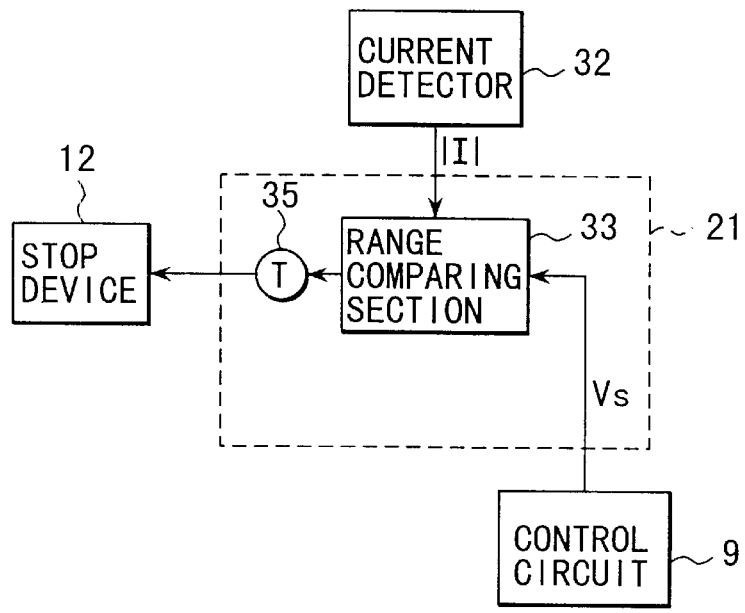
FIG. 9
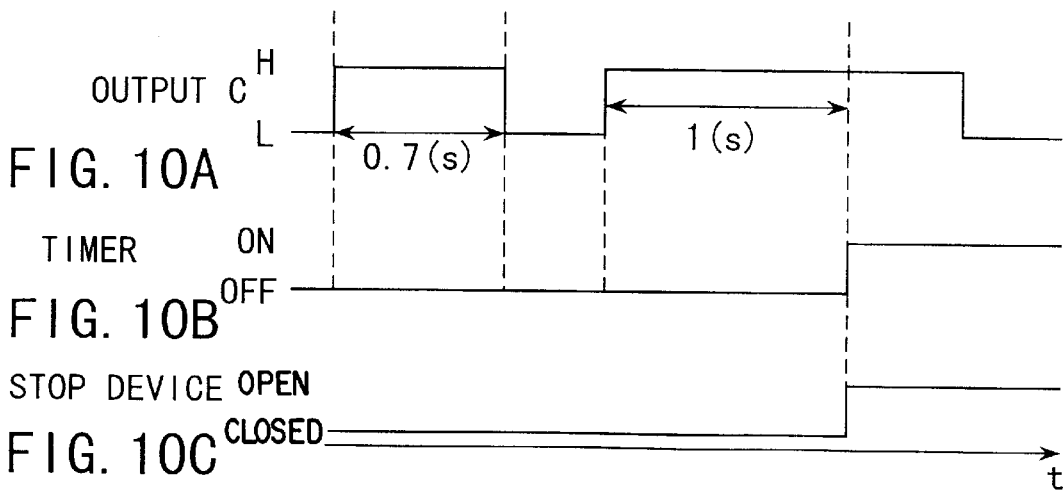
FIG. 10A
FIG. 10B
FIG. 10C

ULTRASONIC OPERATING APPARATUS FOR VIBRATING AN ULTRASONIC VIBRATOR AND PROBE ONLY IN A RANGE CAPABLE OF CONSTANT CURRENT CONTROL AND PLL CONTROL AND A CONTROL METHOD FOR DRIVING ENERGY THEREFOR

BACKGROUND OF THE INVENTION

This invention relates to an ultrasonic operating apparatus and a control method for driving energy therefor, and more particularly to a driving unit for driving an ultrasonic vibrator for use in an ultrasonic operating apparatus or the like in which a medical operation is carried out by transmitting a vibration of an ultrasonic vibrator to a probe, and a control method for driving energy therefor.

In surgery operation, an endoscope has been widely used, for observing a viscus in the celom by inserting its narrow insertion portion therein or as required, and carrying out a diagnostic procedure using a treatment tool inserted in a treatment tool channel of the endoscope.

As for the treatment tool inserted into the treatment tool channel of the endoscope, various types thereof are used depending on a patient and purpose. In recent years, an ultrasonic operating apparatus for carrying out a procedure using an ultrasonic vibration has been used. As the ultrasonic operating apparatus, for example, a surgery ultrasonic knife has been well known, which comprises an ultrasonic vibrator (ultrasonic converter) like, for example, Langevin type vibrator, a probe fit to this ultrasonic vibrator for transmitting a vibration to a distal end thereof and a driving unit for vibrating the ultrasonic vibrator. Some type of the ultrasonic operating apparatus using the aforementioned art recently developed is capable of incision, homostasis, and coagulation.

Generally, a vibration amplitude of the distal end of the probe is proportional to a current for driving the ultrasonic vibrator. The driving unit supplies the ultrasonic vibrator with a current necessary for this vibration amplitude.

However, the impedance of an ultrasonic vibrator actually ultrasonically vibrated changes depending on a load condition applied to each ultrasonic vibrator and each probe. Therefore, to maintain a stable vibration amplitude regardless of a load change in the ultrasonic vibrator, such a driving unit for executing a constant current drive to maintain a current supplied to the ultrasonic vibrator on a constant level has been known.

Here assuming that the impedance of the ultrasonic vibrator is Z, a current for executing the constant current drive is I and a voltage applied to the ultrasonic vibrator by a driving unit for executing the constant current drive is V, the following expression is established.

$$Z=V/I \text{ or } V=IZ \qquad (1)$$

As evident from the expression (1), to drive the ultrasonic vibrator under a constant current, such a requirement is satisfied if a voltage V depending on a change in the impedance Z of the ultrasonic vibrator is applied to the ultrasonic vibrator.

Further, to vibrate the ultrasonic vibrator effectively, it is desired to frequency-drive the ultrasonic vibrator at its resonance point. Therefore, a phase lock loop (PLL) control method in which the resonance point is tracked according to the phase of the current I and voltage V applied to the ultrasonic vibrator has been well known in the conventional art.

On the other hand, miniaturization of a medical apparatus has been progressed in the medical operating field so that the aforementioned ultrasonic driving unit is downsized and its output capacity becomes the smallest level.

If under such a condition, the electrical characteristic of the ultrasonic vibrator changes remarkably, for example the impedance rises remarkably, its applied load exceeds a voltage capacity which can be applied to the ultrasonic vibrator from the driving unit, so that the constant current drive for the ultrasonic vibrator is disabled.

As a result, as evident from the expression (1), a current value supplied to the ultrasonic vibrator drops. Therefore, there occurs a fault in which the ultrasonic vibrator and probe are vibrated at a vibration amplitude lower than a preferred one.

On the other hand, if the impedance of the ultrasonic vibrator drops remarkably, a voltage detected in the driving unit also drops, disabling the PLL control. As a result, there occurs a disadvantage in which its loss is converted to heat or the ultrasonic vibrator and probe are deteriorated due to a distortion.

If an output of the apparatus is continued without maintaining the vibration amplitude of the ultrasonic vibrator and probe at a constant level like the above example, the medical effect may drop. As a medical apparatus, the safety for an operator and patient must be considered by eliminating a possibility of ambustion and electric shock.

To solve the above described problem, Japanese Examined Patent Application No. 2604852 has disclosed a method for preventing a control voltage of the voltage control amplifier (hereinafter referred to as VCA) for changing an amplification factor of an oscillator output to make the drive current constant, from increasing abnormally due to a remarkable change in the electrical characteristic of the ultrasonic vibrator.

However, the above patent has only disclosed a restriction of a upper limit of the amplification factor of the VCA, but has not specified an appropriate range enabling the constant current control and PLL control by considering both those remarkable rise and drop of the impedance of the ultrasonic vibrator.

BRIEF SUMMARY OF THE INVENTION

Accordingly, the present invention has been made in view of the above problems and therefore an object of the invention is to provide an ultrasonic operating apparatus in which an ultrasonic vibrator and probe are vibrated only in a range enabling a constant current control and PLL control so as to always ensure a stabilized performance and improve the safety of the apparatus.

To achieve the above object, according to an aspect of the present invention, there is provided an ultrasonic operating apparatus comprising: an ultrasonic vibrator; a driving energy supply portion for supplying a driving energy for driving the ultrasonic vibrator; a driving energy detecting portion for detecting a driving energy supplied to the ultrasonic vibrator from the driving energy supply portion; a determining portion for determining whether or not the ultrasonic vibrator is driven normally depending on whether or not a driving energy detected by the driving energy detecting portion is in a predetermined range; and a stop portion for stopping a supply of the driving energy to the ultrasonic vibrator if it is determined that the ultrasonic vibrator is not driven normally.

Further, according to another aspect of the present invention, there is provided a method for controlling driving energy supplied to an ultrasonic vibrator of an ultrasonic operating apparatus comprising: a driving energy detecting step for detecting a driving energy supplied to the ultrasonic vibrator; a determining step for determining whether or the ultrasonic vibrator is driven normally depending on whether or not the driving energy detected in the driving energy detecting step is in a predetermined range; and a stop step for stopping a supply of the driving energy to the ultrasonic vibrator when it is determined that the ultrasonic vibrator is not driven normally.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

FIG. 7 is a diagram for explaining how OUTPUT A, OUTPUT B and OUTPUT C change with respect to the magnitude |I| of current components input to comparing devices 33a, 33b;

FIG. 9 is a diagram showing a structure of an ultrasonic operating apparatus according to a second embodiment of the present invention;

FIGS. 10A, 10B and 10C are time charts for explaining an operation of the second embodiment;

DETAILED DESCRIPTION OF THE INVENTION

Figure 1:
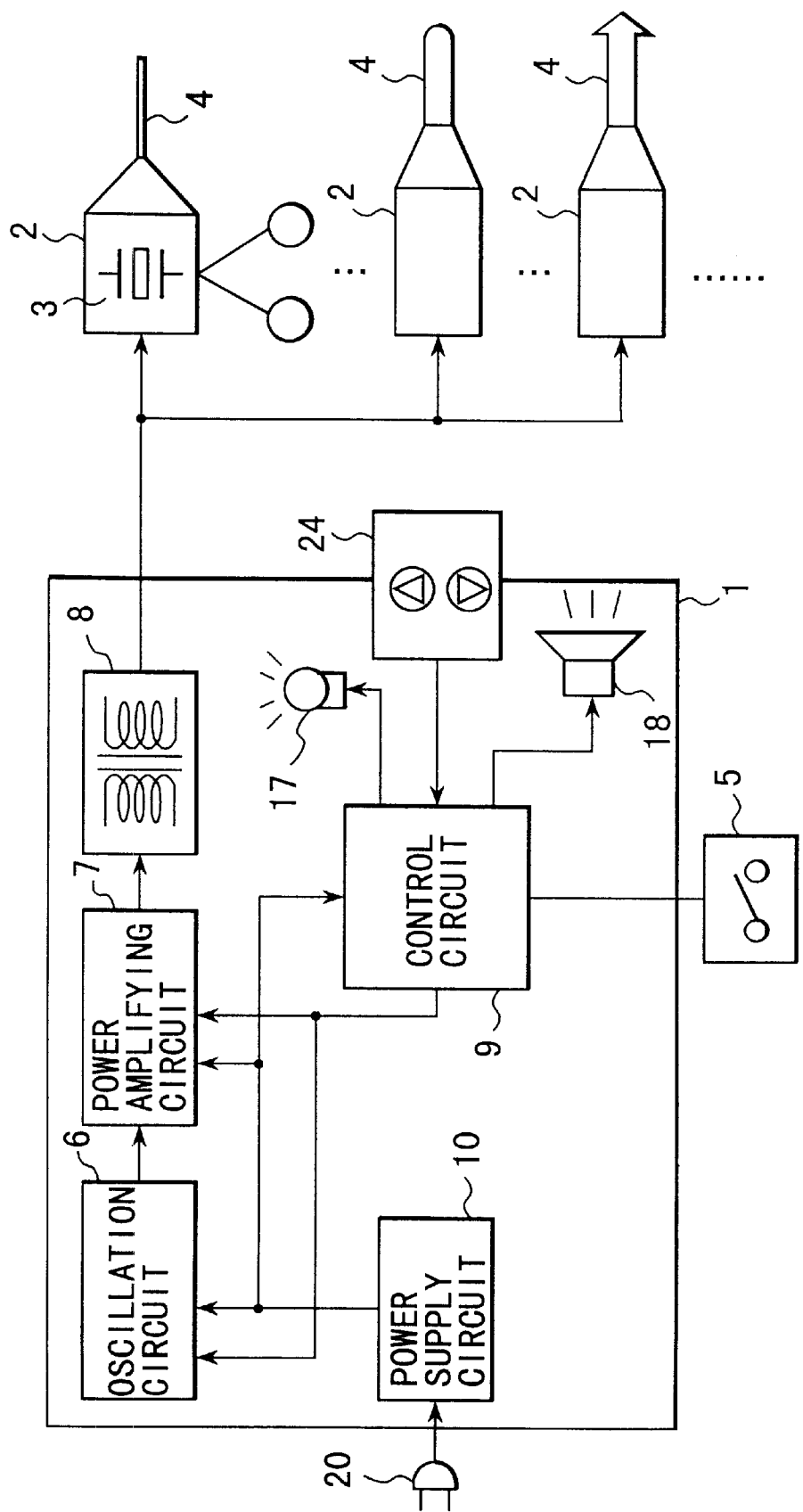
FIG. 1 is a diagram showing a general structure of an ultrasonic operating apparatus.

Hereinafter, the embodiment of the present invention will be described in detail with reference to the accompanying drawings. FIG. 1 is a diagram showing a general structure of an ultrasonic operating apparatus. To an ultrasonic driving unit 1 is connected a hand piece 2 containing an ultrasonic vibrator 3 which is vibrated receiving a driving energy of the ultrasonic driving unit 1 and a switch for determining whether or not a driving energy is supplied to this hand piece 2, for example, a foot press type operation switch 5. A probe 4 which is a distal end for treatment is removably fit to the hand piece 2.

The aforementioned ultrasonic driving unit 1 has the following internal structure. That is, an oscillation circuit 6 is provided as an oscillation circuit for generating a driving signal so as to supply a resonance frequency to the ultrasonic vibrator 3, this oscillation circuit generating an oscillation frequency signal causing an ultrasonic vibration, for example sine waves of 20–60 KHz. This oscillation circuit 6 may contain a frequency control circuit based on phase locked loop (PLL) or the like for tracking a resonance point of the ultrasonic vibrator 3 according to a relation in phase of a voltage applied to the ultrasonic vibrator 3 and a current flowing therein. Further, a power amplifying circuit 7 is provided for amplifying an oscillation frequency signal from the oscillation circuit 6. The power amplifying circuit 7 constitutes a driving energy supply portion with the oscillation circuit 6, amplifies sine wave generated in the oscillation circuit 6 and supplies a driving energy to the ultrasonic vibrator 3 with an insulation through an output transformer 8.

Further, a control circuit 9 for controlling an operation of each circuit and a power supply circuit 10 for supplying a power to each circuit are provided. The power circuit 10 is supplied with a power from a commercial power source and connected to a power plug 20. A setting portion 24 for setting a current component ratio (hereinafter referred to as setting value) of a driving energy to the ultrasonic vibrator 3 is provided and the setting value is transmitted to the control circuit 9. To the control circuit 9 is connected a display portion 17 for displaying a setting value set by the setting portion 24 or other information and a speaker 18 for making a sound to carry out the aforementioned display.

Figure 2:
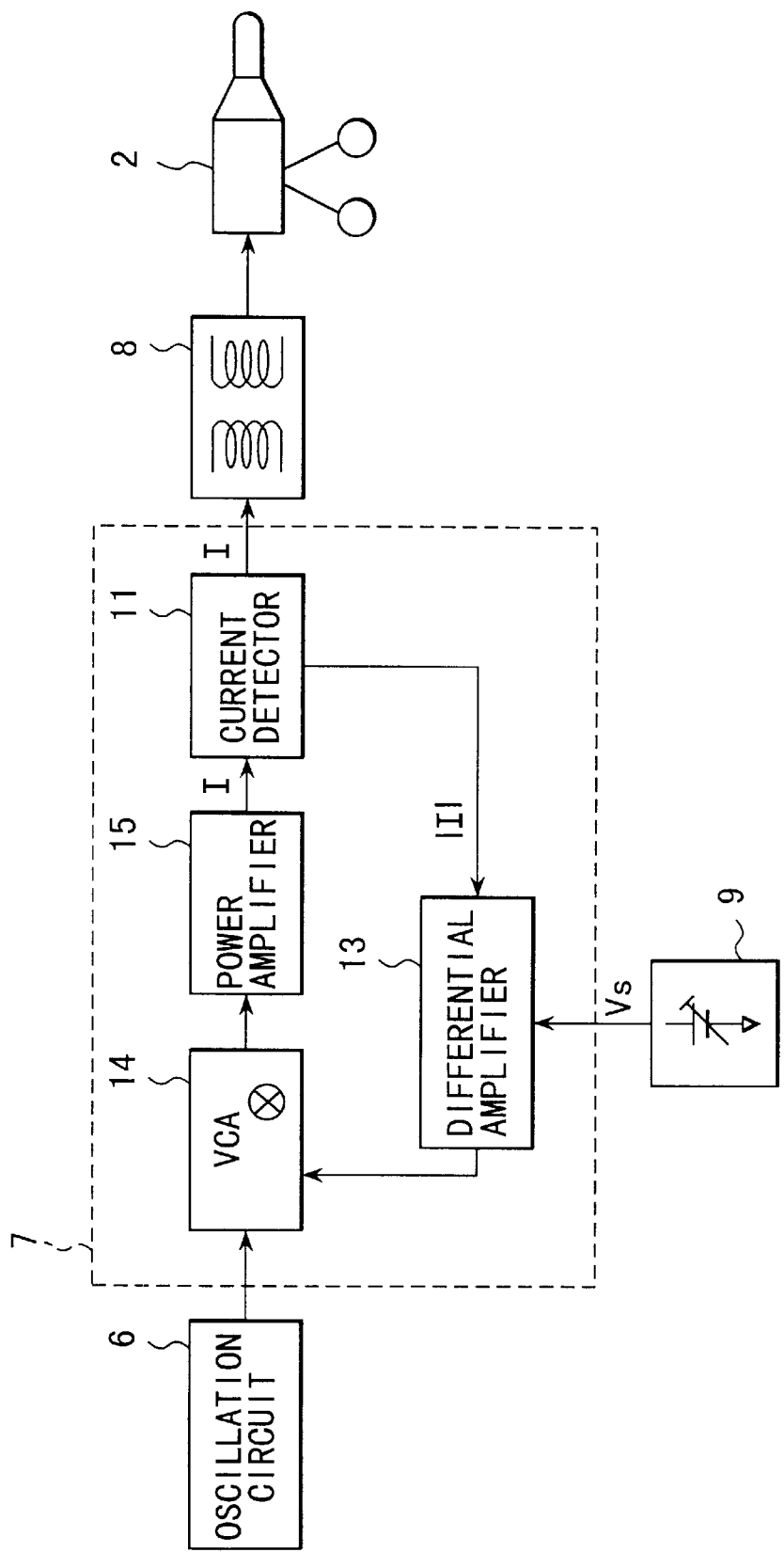
FIG. 2 is a diagram showing a detailed structure of a power amplifying circuit 7 of FIG. 1.

FIG. 2 is a diagram showing a structure of the power amplifying circuit 7 of FIG. 1 in detail. As shown in FIG. 2, the power amplifying circuit 7 comprises a current detector 11, a differential amplifier 13, a VCA 14 which is a multiplier, and a power amplifier 15.

An oscillation frequency signal transmitted from the oscillation circuit 6 is input to the power amplifier 15 through the VCA 14 and output to the hand piece 2 through the output transformer 8. The current detector 11 is provided between the output transformer 8 and power amplifier 15, the current detector detecting and rectifying a current component I of a driving energy output from the power amplifier 15 and then inputting the current component having a magnitude |I| to an input end of the differential amplifier 13. Further, the setting value set by the setting portion 24 is processed by the control portion 9 to produce a reference voltage Vs and this reference voltage Vs is input to the other input end of the differential amplifier 13.

The differential amplifier 13 carries out differential amplification so as to make the aforementioned two input values equal to each other and feeds back its change rate to the VCA 14. The VCA 14 multiplies a feed back signal by an oscillation frequency signal from the oscillation circuit 6 and transmits its result to the power amplifier 15.

Because an amplification factor of the power amplifier 15 is controlled by such a feed back loop, a driving energy having a constant current component can be supplied to the hand piece 2.

Figure 3:
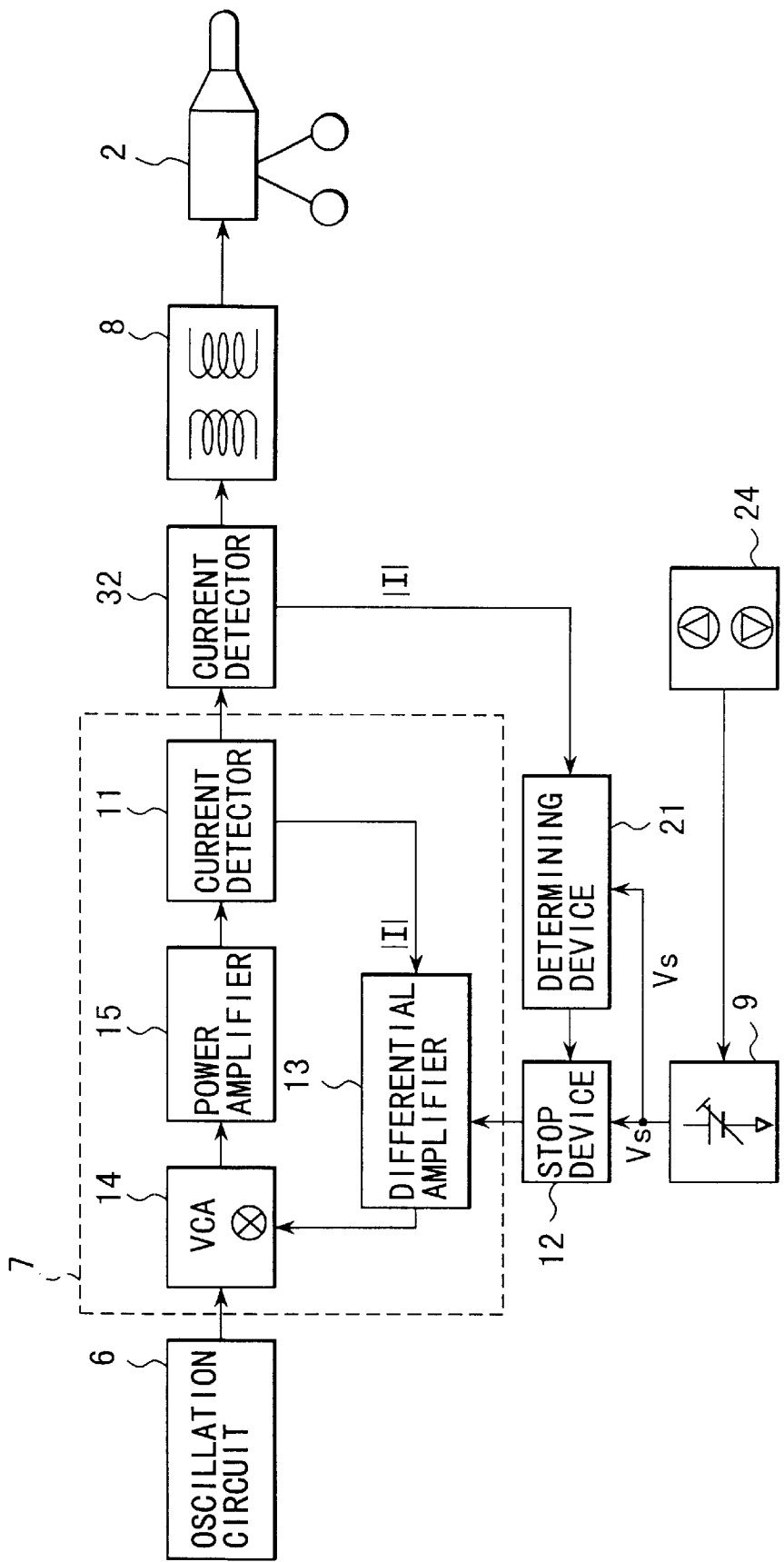
FIG. 3 is a diagram showing a structure of an ultrasonic operating apparatus according to a first embodiment of the present invention.

FIG. 3 is a diagram showing a structure of the ultrasonic operating apparatus according to a first embodiment of the present invention. In addition to the structure of FIG. 1, a second current detector 32 for detecting a driving energy is provided between the current detector 11 and output transformer 8, and a stop device (stop portion) 12 constituted of a switch or the like is provided between the differential amplifier 13 and control circuit 9, and a determining device (determining portion) 21 is provided between the current detector 32 and stop device 12. The determining device 21 is connected to the control circuit 9.

With such a structure, the current detector 32 extracts a magnitude |I| of current component from driving energy like the current detector 11. The magnitude |I| of the current component extracted by the current detector 32 is input to the determining device 21. The stop device 12 operates to shut down the reference voltage Vs input to the differential amplifier 13 from the control circuit 9 according to a result of determination of the determining device 21.

Figure 4:
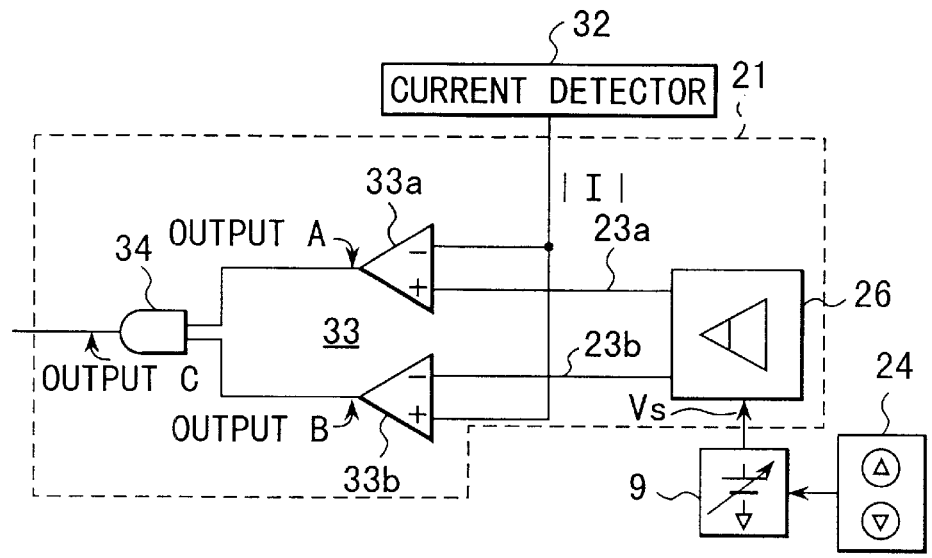
FIG. 4 is a diagram showing a detailed structure of a determining device 21 of FIG. 3.

FIG. 4 is a diagram showing a structure of the determining device 21 of FIG. 3 in detail. As shown in FIG. 4, the determining device 21 comprises a voltage converting portion 26 for converting the reference voltage Vs from the control circuit 9, a range comparing portion 33 including a pair of comparing devices 33a, 33b and an AND circuit 34 for receiving outputs from the comparing devices 33a, 33b and carrying out logical AND therebetween. In this case, the magnitude |I| of current component is input to each of first input terminals of the comparing devices 33a, 33b from the current detector 32 and an output of the voltage converting portion 26 is input to each of the second input terminals.

In this structure, the reference voltage Vs supplied to the voltage converting portion 26 from the control circuit 9 can be changed depending on the setting of the setting portion 24. The voltage converting portion 26 amplifies the reference voltage Vs from the control circuit 9 based on a predetermined proportional relation and inputs reference voltages 23a, 23b to the second input terminals of the comparing devices 33a, 33b. The aforementioned magnitude |I| of the current component from the current detector 32 is input to the first input terminals.

When the driving energy is being supplied to the hand piece 2 according to the setting value set by the setting portion 24, a relation between the magnitude |I| of current component extracted by the current detector 32 and the reference voltages 23a, 23b is expressed in the following formula (2).

$$23a > |I| > 23b \quad (2)$$

Figure 5:
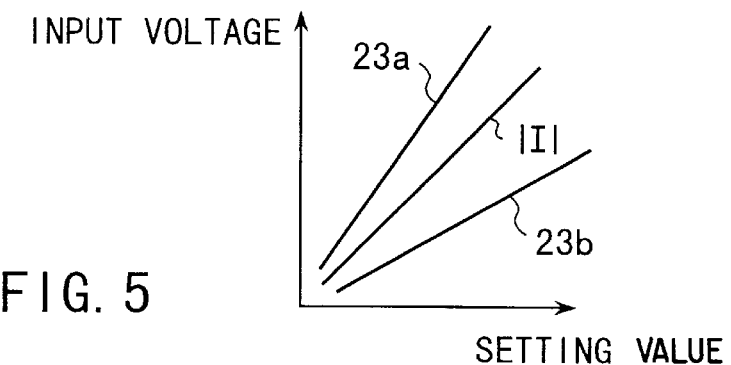
FIG. 5 is a diagram showing a relation between input voltage and setting value for use in determining whether or not the reference voltages 23a, 23b and magnitude |I| of a current component are in a predetermined relation.
Figure 6A:
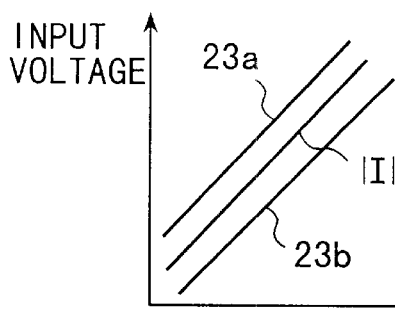
FIGS. 6A and 6B are diagrams for showing another relation between the input voltage and setting value.
Figure 6B:
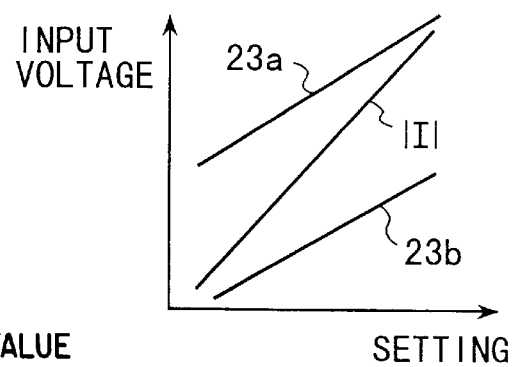

To determine whether or not this relation is satisfied, a relation between input voltage and setting value as shown in FIG. 5 may be used. Or a relation shown in FIG. 6A or 6B may be used.

Here assume that determining results of the comparing devices 33a, 33b are OUTPUT A, OUTPUT B and a result of logical AND of the two determining results by the AND circuit 34 is OUTPUT C. FIG. 7 shows how the OUTPUT A, OUTPUT B and OUTPUT C change with respect to the magnitude |I| of the current component input to the comparing devices 33a, 33b.

If the magnitude |I| of current component of driving energy supplied to the hand piece 2 becomes excessively large so that |I|>23a is formed, OUTPUT A becomes "L" level, so that OUTPUT C also becomes "L" level. Likewise, if the magnitude |I| of current component of a driving energy supplied to the hand piece 2 becomes excessively small so that |I|<23b is formed, OUTPUT B becomes "L" level so that OUTPUT C also becomes "L" level.

As a result, only when the magnitude |I| of current component is 23a>|I|>23b, OUTPUT C becomes "H" level. Therefore, when OUTPUT C is in "L" level, that is, the magnitude |I| of current component becomes excessively large or excessively small, a driving stop signal is transmitted to the stop device 12 so as to shut down the reference voltage Vs and then the supply of the driving energy to the output transformer 8 is stopped.

Figure 8:
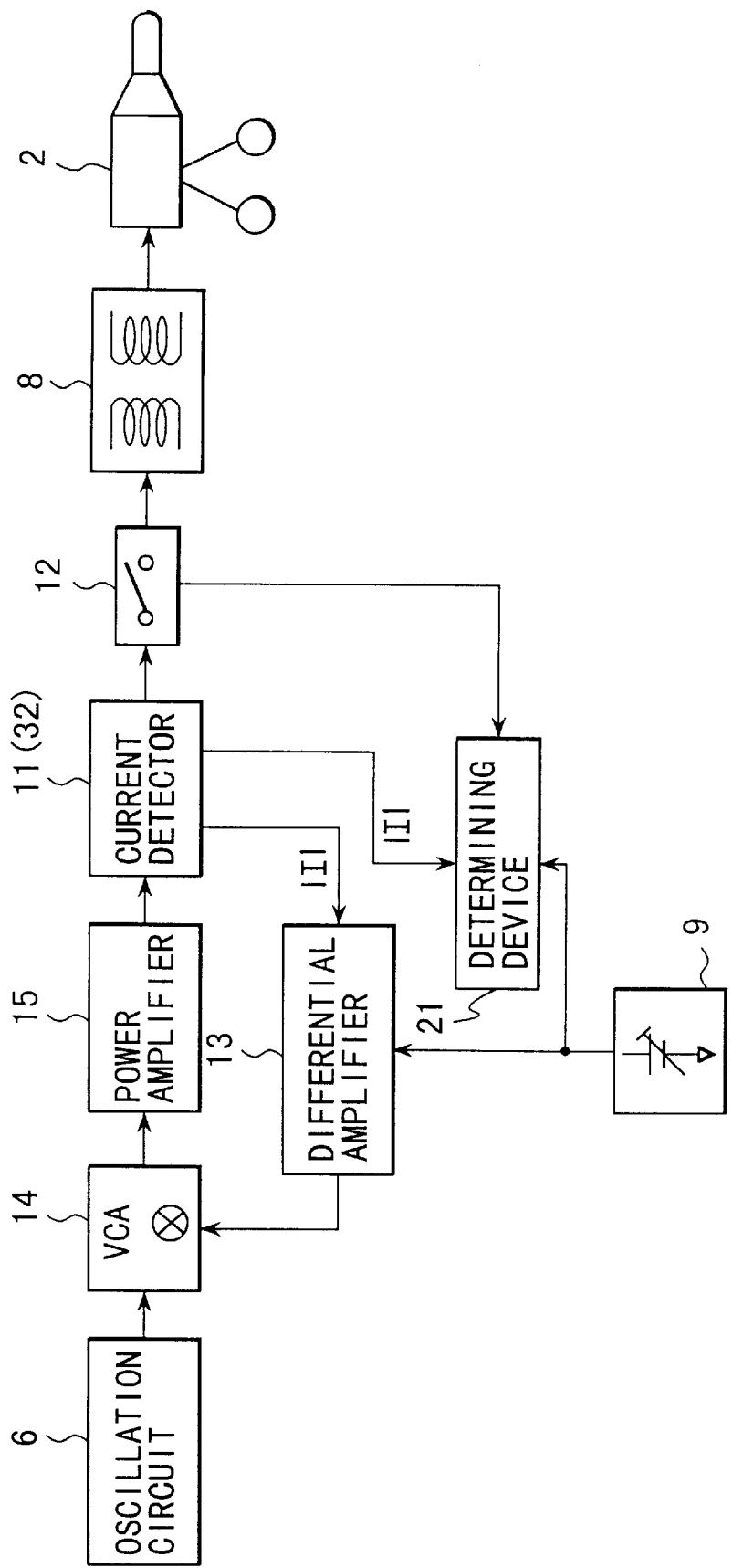
FIG. 8 is a diagram for showing an example of a structure in which a stop device 12 is disposed between a current detector 32 and an output transformer 8.

Even if the stop device 12 is located between the current detector 32 and output transformer 8 as shown in FIG. 8, the same effect can be achieved. In FIG. 8, the current detector 32 serves for the current detector 11 at the same time. Further although not shown here, it is needless to say that the same effect is achieved even if the stop device 12 is disposed at any position between the oscillation circuit 6, VCA 14, power amplifier 15, and current detector 11. If a path from the output transformer 8 to the vibrator 3 contained in the hand piece 2 is broken so that a driving energy cannot be supplied, although not shown here, the same effect can be obtained because the magnitude |I| of current component becomes excessively small.

As described above, according to the first embodiment, the detecting portion for detecting the magnitude |I| of current component of a driving energy in the ultrasonic vibrator is provided for determining whether or not a detection result exists in a constant range relative to a predetermined setting value, and if it does not exist within such a range, the supply of a driving energy to the hand piece 2 is stopped. As a result, even if electrical characteristic of the ultrasonic vibrator changes considerably so that the current component of the driving energy of the ultrasonic vibrator changes abnormally, this abnormal current component is not supplied to the ultrasonic vibrator. Therefore, the current component of the driving energy is restricted to a constant range during a supply of the driving energy, so that the safety can be assured.

Next, a second embodiment of the present invention will be described with reference to FIGS. 9, 10A, 10B, and 10C. The second embodiment indicates another structure of the determining device 21 described in the first embodiment. As shown in FIG. 9, this determining device 21 comprises a range comparing portion 33 and a timer 35. The timer 35 is constituted of, for example, a timer relay and is turned on only if an "H" level signal from the range comparing portion 33 is input for more than 1 second (FIGS. 10A, 10B). That is, even if the OUTPUT C of the range comparing portion 33 becomes "H" level, if the "H" level signal is input for less than 1 second, the timer relay contact point remains OFF. When "H" level of OUTPUT C exceeds 1 second, the timer relay contact point is turned ON and correspondingly, as shown in FIG. 10C, a switch of the stop device 12 is opened thereby stopping a supply of the reference voltage Vs to the differential amplifier 13.

As described above, according to the second embodiment, a detecting portion for detecting the current component of the driving energy of the ultrasonic vibrator is provided and further to determine whether or not a detection result exists in a predetermined range relative to a desired setting value, a monitor portion for monitoring a continuity of that value with a passage of time is provided. Therefore, an effect of preventing a malfunction due to electric noise is added to the effect of the first embodiment, so that the safety can be improved further.

Figure 11:
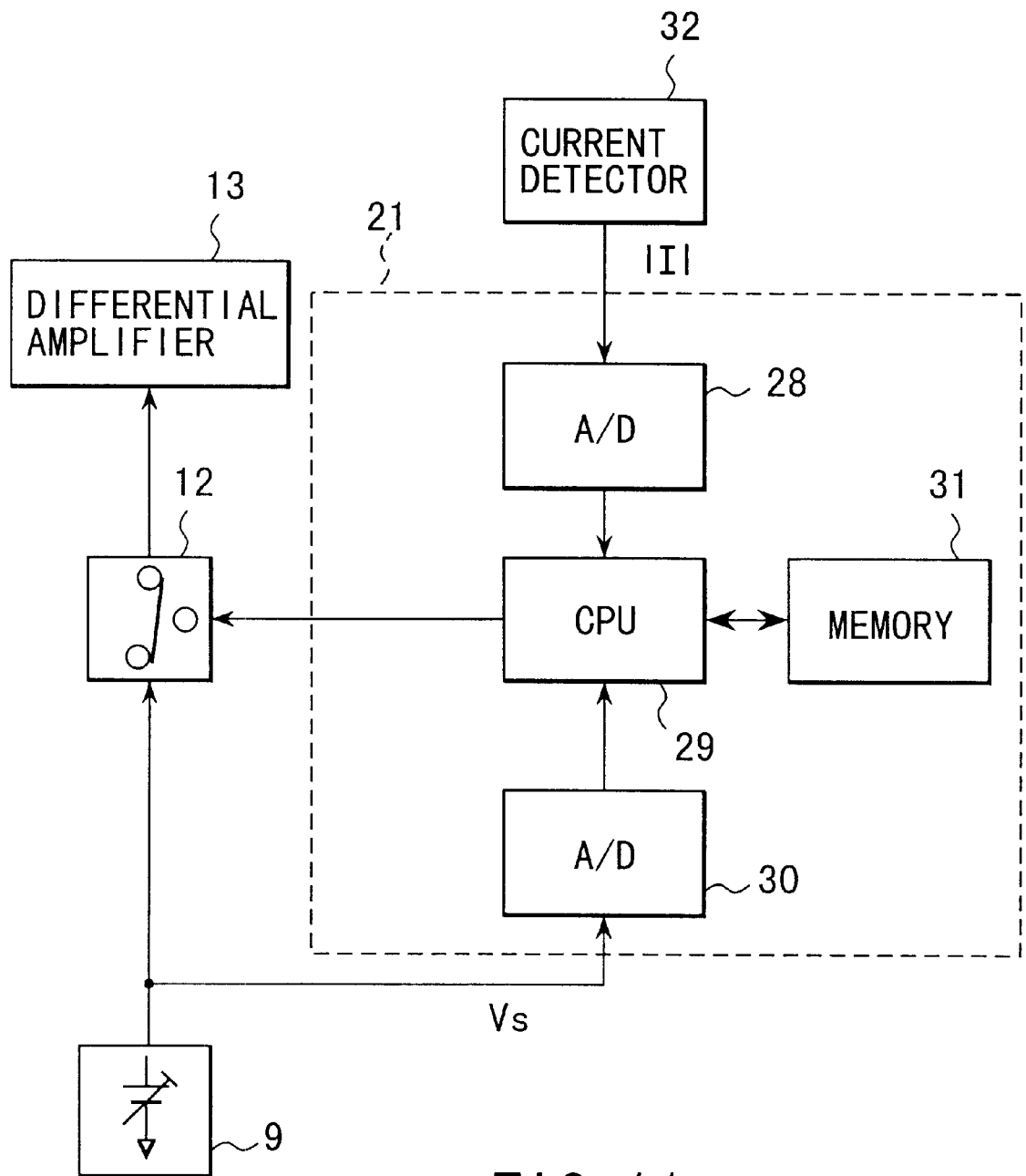
FIG. 11 is a diagram showing a structure of an ultrasonic operating apparatus according to a third embodiment.

A third embodiment of the present invention will be described with reference to FIGS. 11, 12. The third embodiment indicates still another structure of the determining device 21 described in the first embodiment. As shown in FIG. 11, the determining device 21 comprises an A/D converter 28 for converting the magnitude |I| of the current component to digital signals, an A/D converter 30 for converting the reference voltage Vs from the control circuit 9 to digital signal, an arithmetic operation portion (CPU) 29 for carrying out digital operation based on the digital signals from these two A/D converters 28, 30, and a memory 31 writably containing a program and data necessary for the arithmetic operation of the arithmetic operation portion 29.

Figure 12:
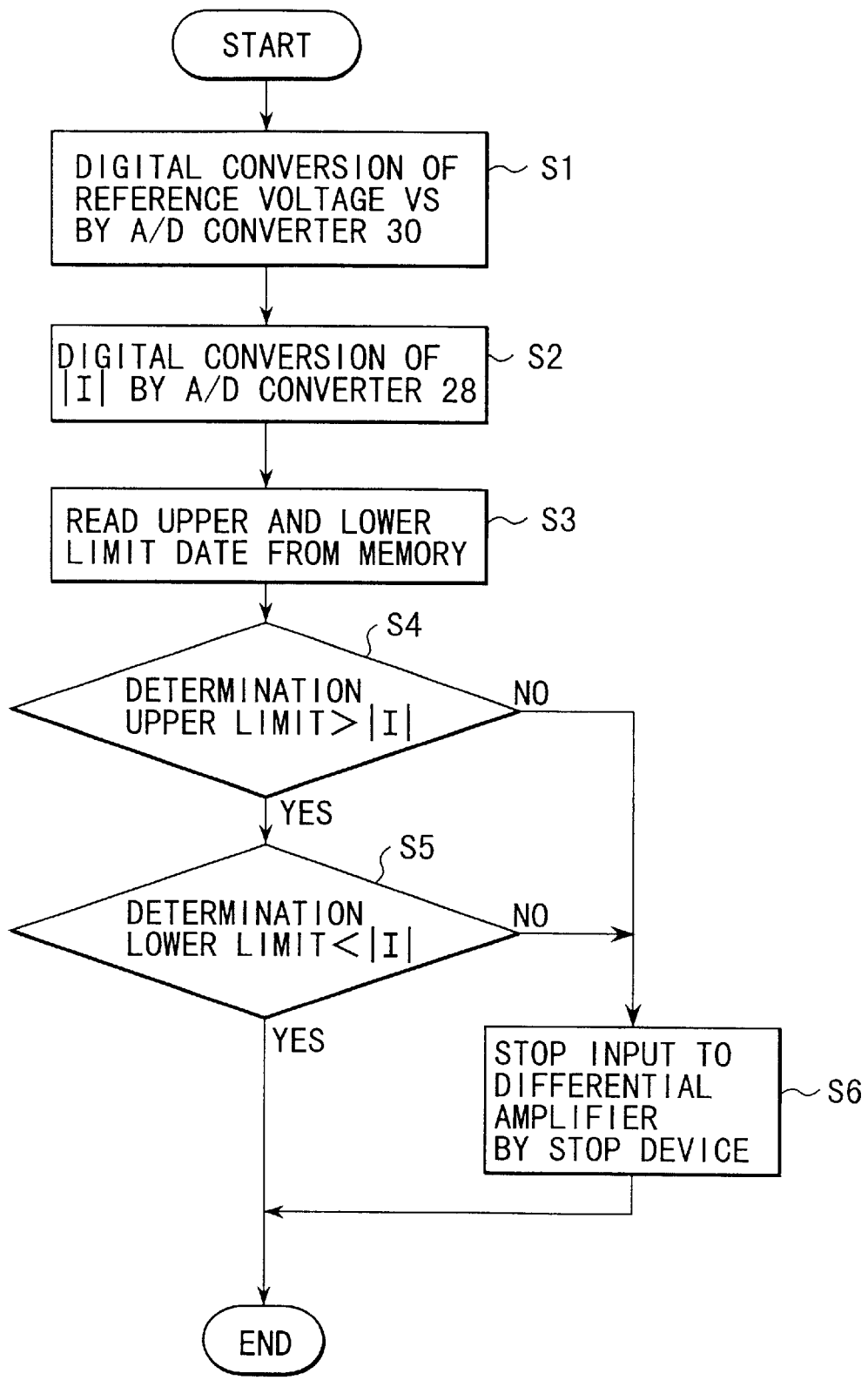
FIG. 12 is a time chart for explaining an operation of the third embodiment.

FIG. 12 is a flow chart for explaining a determining operation of the arithmetic operation portion 29 for the magnitude |I| of the current component. First, the A/D converter 30 converts the reference voltage Vs from the control circuit 9 to digital signals (step S1) and the A/D converter 28 converts the magnitude |I| of the current component from the current detector 32 to digital signals (step S2). Next, upper and lower limit data of a threshold for determining data held in the memory 31 with respect to the reference voltage Vs are read (step S3). Then, by comparing the upper and lower limit values of the threshold with the magnitude |I| of the current component, whether or not the |I| exists in a range determined by the upper and lower limit values of the threshold is determined (steps S4, S5). If the magnitude |I| does not exist in the aforementioned range, the stop device 12 is opened so as to stop the reference voltage Vs to be supplied to the differential amplifier 13 (step S6).

As described above, according to the third embodiment, the detecting portion for detecting the current component of the driving energy of the ultrasonic vibrator is provided and a portion for determining whether or not a detection result exists in a predetermined range relative to a desired setting value is constituted of the digital arithmetic operation portion. Therefore, in addition to the effect of the first embodiment, a threshold in which the setting value of the driving energy is a variable, can be changed easily, thereby preventing an expansion of the circuit.

Figure 13:
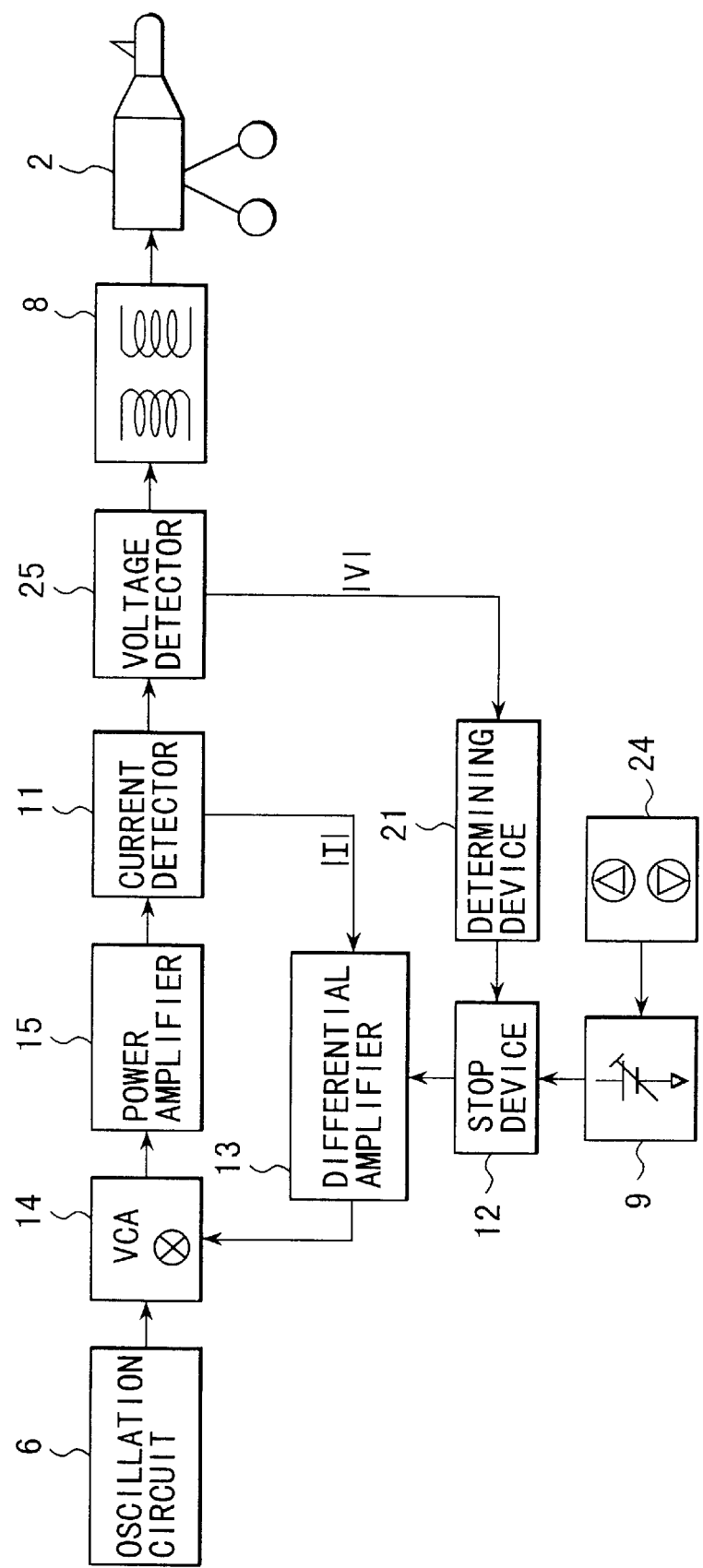
FIG. 13 is a diagram showing a structure of an ultrasonic operating apparatus according to a fourth embodiment of the present invention.

A fourth embodiment of the present invention will be described with reference to FIGS. 13, 14. In the fourth embodiment, a voltage detector 25 is provided instead of the current detector 32 of the first embodiment.

As described previously, when the driving energy from the power amplifier 15 is on the highest voltage or the lowest voltage enabling the PLL control, the driving energy is not supplied to the hand piece 2 according to the setting value set by the setting portion 24. The fourth embodiment proposes a counter-measure for such a condition.

Figure 14:
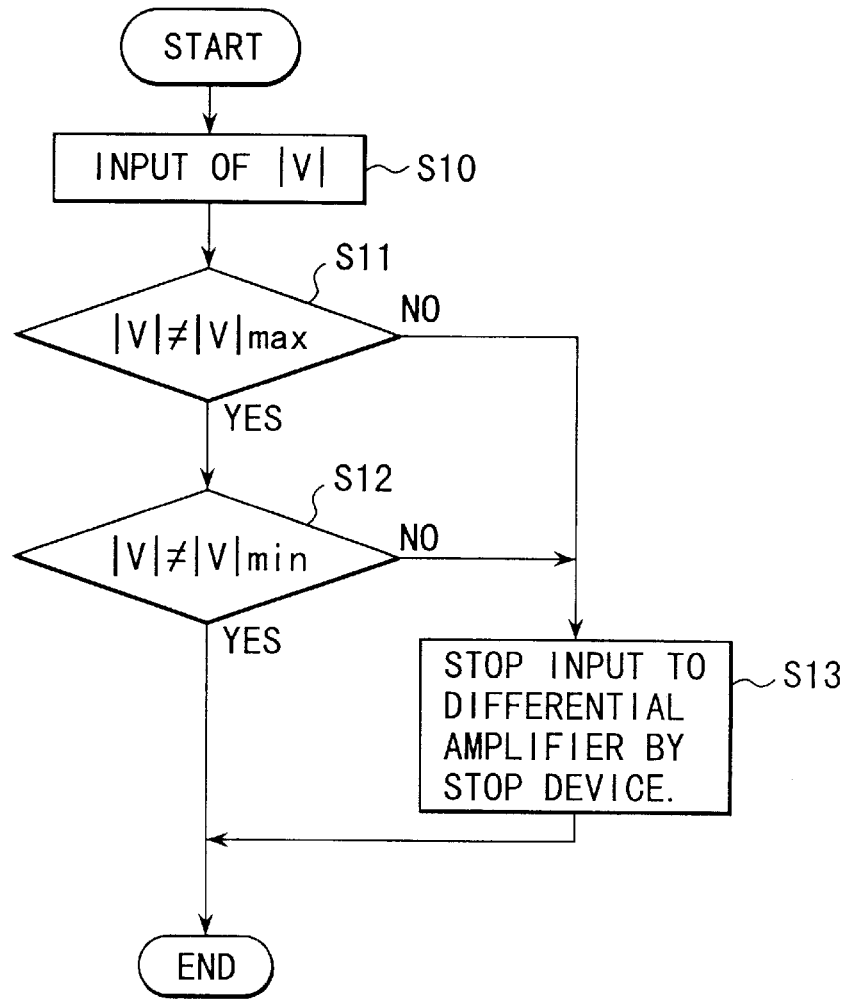
FIG. 14 is a flow chart for explaining an operation of the fourth embodiment.

FIG. 14 is a flow chart for explaining a determining operation of the determining device 21 for the magnitude |V| of the voltage component.

First of all, the magnitude |V| of a voltage component of driving energy detected by the voltage detector 25 is input (step S19). Then, whether or not the magnitude |V| of the voltage component is the maximum value |V| or minimum value |V| is determined (steps S11, S12). If it is the maximum value or minimum value, a supply of the reference voltage Vs to the differential amplifier 13 is stopped by the stop device 12.

As described above, according to the fourth embodiment, a detecting portion for detecting the voltage component of the driving energy of the ultrasonic vibrator is provided so as to determine whether or not the driving energy is being supplied according to a setting value, depending on which is the detected voltage, the maximum value or minimum value. Therefore, with a further simplified structure as compared to the first embodiment, the same effect can be obtained.

Although the above described respective embodiments are so constructed that the reference voltage Vs can be arbitrarily changed by the setting portion 24, this reference voltage Vs may be fixed.

Figure 15:
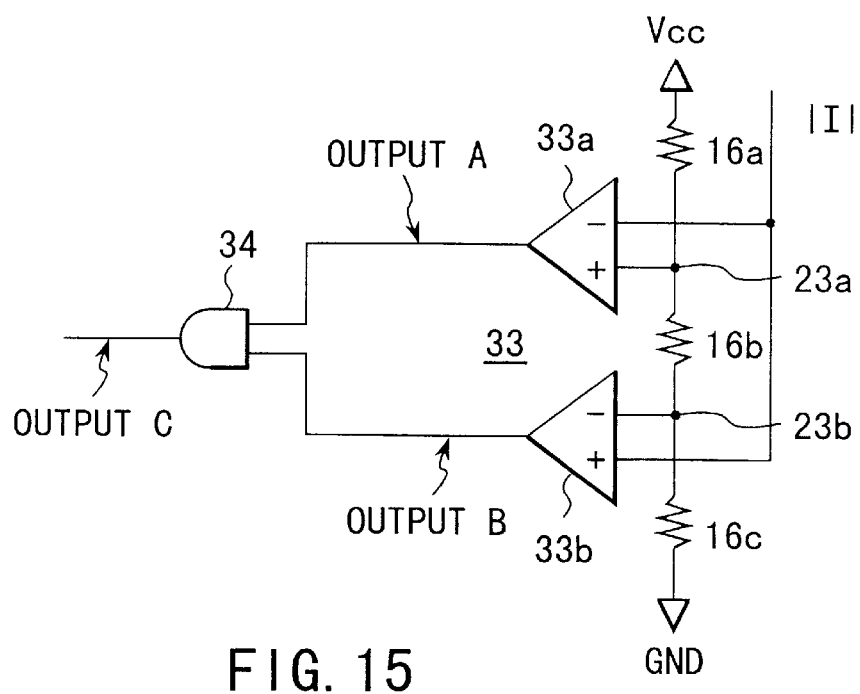
FIG. 15 is a diagram showing a structure of a determining device according to a fifth embodiment of the present invention.

FIG. 15 indicates an example of a structure of the determining device 21 in which the reference voltage Vs is fixed, according to a fifth embodiment of the present invention. This determining device 21 comprises voltage dividers 16a, 16b, 16c constituted of a resistor each, a range comparing portion 33 containing a pair of comparing devices 33a, 33b, and an AND circuit 34. The voltage dividing reference voltages 23a(V), 23b(V) divided by resistance of the voltage dividers 16a, 16b, 16c are input to the comparing devices 33a, 33b. The voltage dividing reference voltages 23a(V), 23b(V) correspond to the aforementioned reference voltage Vs.

With such a structure, the same effect as the first embodiment can be obtained. Although the fifth embodiment is not capable of changing the setting value, the function for converting the setting portion 24 and the setting value to the reference voltage Vs are not necessary.

As described above, according to the present invention, even if the current component of the driving energy of the ultrasonic vibrator changes abnormally, this abnormal current component is not supplied to the ultrasonic vibrator. Therefore, the current component of the driving energy is restricted to a predetermined range during the supply of the driving energy.

Therefore, it is possible to effectively prevent the driving circuit system and ultrasonic vibrator from being damaged by application of a current larger than their resistance properties and further the safety to an object and organism can be assured so that a desired medical effect can be obtained stably.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic operating apparatus comprising:
   an ultrasonic vibrator;
   a driving energy supply portion for supplying a driving energy for driving the ultrasonic vibrator;
   an energy setting portion for setting a value for the driving energy to be supplied from the driving energy supply portion;
   a driving energy detecting portion for detecting a driving energy supplied to the ultrasonic vibrator from the driving energy supply portion;
   a comparing portion for comparing the driving energy detected by the driving energy detecting portion with a value set by the energy setting portion and controlling, on the basis of results of comparison, an amount of driving energy supplied by the driving energy supply portion;
   a determining portion for determining whether or not the ultrasonic vibrator is driven normally depending on whether or not a driving energy detected by the driving energy detecting portion is in a predetermined range, said determining portion including a range comparing portion for comparing the driving energy detected by the driving energy detecting portion with a comparison reference value that specifies a comparison range indicating that the ultrasonic vibration is driven normally, and said determining portion determining whether or not the ultrasonic vibrator is driven normally on the basis of a level of an output signal from the range comparing portion; and a stop portion for stopping a supply of the driving energy to the ultrasonic vibrator if it is determined that the ultrasonic vibrator is not driven normally.

2. An ultrasonic operating apparatus according to claim 1, wherein the range comparing portion comprises:

a pair of comparing devices each having a first input terminal for receiving the detected driving energy and a second input terminal for receiving the comparison reference value, said pair of comparing devices each producing an output; and an AND circuit for carrying out a logical AND function between the outputs produced by the pair of the comparing devices.

3. An ultrasonic operating apparatus according to claim 1, further comprising a reference value setting portion for setting the comparison reference value arbitrarily.

4. An ultrasonic operating apparatus according to claim 1, wherein the comparison reference value is a fixed value.

5. An ultrasonic operating apparatus according to claim 4, wherein the fixed value is a voltage dividing reference voltage divided by a resistance of a plurality of voltage dividers.

6. An ultrasonic operating apparatus according to claim 1, further comprising a timer for monitoring a signal level of an output from the range comparing portion with a passage of time, the timer determining whether or not the driving energy is in a predetermined range depending on whether the signal level continues for a predetermined interval of time.

7. An ultrasonic operating apparatus according to claim 1, wherein the range comparing portion converts the detected driving energy and comparison reference value to a digital value for comparison thereof.

8. An ultrasonic operating apparatus according to claim 1, wherein the driving energy detecting portion detects a current component of the driving energy from the driving energy supply portion.

9. An ultrasonic operating apparatus according to claim 1, wherein the driving energy detecting portion detects a voltage component of the driving energy from the driving energy supply portion.

10. A method for controlling driving energy supplied to an ultrasonic vibrator of an ultrasonic operating apparatus, comprising:

a driving energy detecting step for detecting a driving energy supplied to the ultrasonic vibrator;

a comparing step for comparing the driving energy detected at the driving energy detecting step with a value predetermined by an energy setting portion, and controlling the driving energy supplied to the ultrasonic vibrator on the basis of the results of comparison;

a determining step for determining whether or not the ultrasonic vibrator is driven normally depending on whether or not the driving energy detected in the driving energy detecting step is in a predetermined range, said determining step including a range comparing step in which the driving energy detected at the driving energy detecting step is compared with a comparison reference value specifying a comparison range indicating that the ultrasonic vibration is driven normally, wherein the ultrasonic vibrator is determined as being driving normally or not on the basis of a level of a signal output at the range comparing step; and a stop step for stopping a supply of the driving energy to the ultrasonic vibrator when it is determined that the ultrasonic vibrator is not driven normally.

* * * * *